US00PP25914P3

(12) United States Plant Patent
Dirr

(10) Patent No.: US PP25,914 P3
(45) Date of Patent: Sep. 22, 2015

(54) ***VITEX* PLANT NAMED 'PIIVAC-I'**

(50) Latin Name: ***Vitex agnus-castus* L.**
Varietal Denomination: PIIVAC-I

(71) Applicant: Matthew A. Dirr, Watkinsville, GA (US)

(72) Inventor: Matthew A. Dirr, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 148 days.

(21) Appl. No.: 13/998,259

(22) Filed: Oct. 16, 2013

(65) Prior Publication Data

US 2015/0106984 P1 Apr. 16, 2015

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Anne Grunberg
(74) *Attorney, Agent, or Firm* — Lathrop & Gage LLP

(57) ABSTRACT

A new and distinct cultivar of *Vitex* plant named 'PIIVAC-I', characterized by its compact, rounded to upright-spreading growth habit, dark green foliage, dark bluish purple flowers, and resistance to leaf spot.

2 Drawing Sheets

Genus and species of plant claimed: *Vitex agnus-castus* L.
Variety denomination: 'PIIVAC-I'.

BACKGROUND OF THE INVENTION

The present invention relates to a new and distinct cultivar of *Vitex* plant, botanically known as *Vitex agnus-castus* L., commonly known as chastetree, and hereinafter referred to by the cultivar name 'PIIVAC-I'. 'PIIVAC-I' is grown primarily as an ornamental for landscape use and for use as a potted plant.

'PIIVAC-I' originated from an open-pollination of an unnamed and unpatented seedling selection of *Vitex agnus-castus* growing in Watkinsville, Ga. in 2009. The cultivar 'PIIVAC-I' originated and was selected in a cultivated environment in Watkinsville, Ga. from the progeny of this open-pollination by continued evaluation for growth habit, foliage and flower characteristics.

Asexual reproduction of 'PIIVAC-I' by stem cuttings in Watkinsville, Ga. since 2011 has shown that all the unique features of this new *Vitex*, as herein described, are stable and reproduced true-to-type through successive generations of such asexual propagation.

SUMMARY OF THE INVENTION

Plants of the new cultivar 'PIIVAC-I' have not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'PIIVAC-I' from all other varieties in commerce known to the inventor.

1. Compact, rounded to upright-spreading growth habit;
2. Dark green foliage;
3. Dark bluish purple flowers;
4. Resistance to leaf spot.

'PIIVAC-I' is distinguished from its female parent by its growth habit and flower color. 'PIIVAC-I' has an overall smaller, compact, rounded to upright-spreading growth habit and dark bluish purple flowers, whereas its female parent has an overall larger, rounded to upright-spreading growth habit and lighter purple flowers.

'PIIVAC-I' can be compared to 'Shoal Creek' (unpatented), but differs in the following characteristics. 'PIIVAC-I' has an overall smaller and more compact growth habit than 'Shoal Creek'. 'PIIVAC-I' has smaller foliage than 'Shoal Creek'. 'PIIVAC-I' has smaller inflorescences and darker flower color than 'Shoal Creek'.

BRIEF DESCRIPTION OF THE DRAWINGS

The accompanying color photographs illustrate the flower and foliage characteristics and the overall appearance of 'PIIVAC-I', showing the colors as true as it is reasonably possible to obtain in color reproductions of this type. Colors in the photographs may differ slightly from the color values cited in the detailed botanical description which accurately describe the colors of the new *Vitex*.

DETAILED DESCRIPTION

Figure 1:
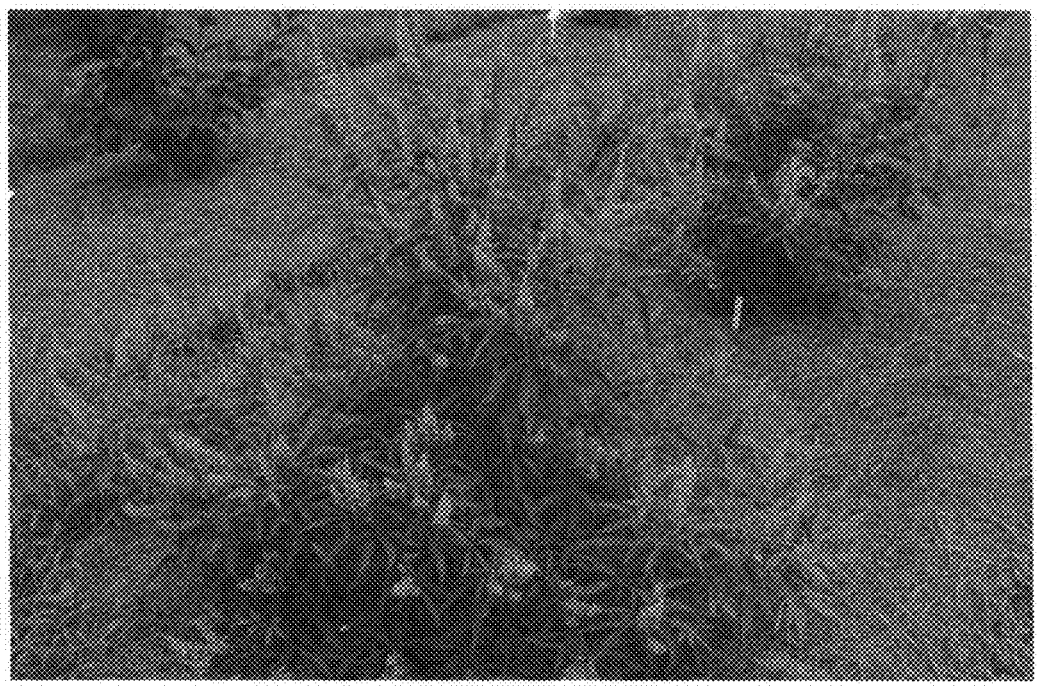
FIG. 1 Illustrates a comparison of 'PIIVAC-I' (foreground) and 'Shoal Creek' (background) planted in the ground.
Figure 2:
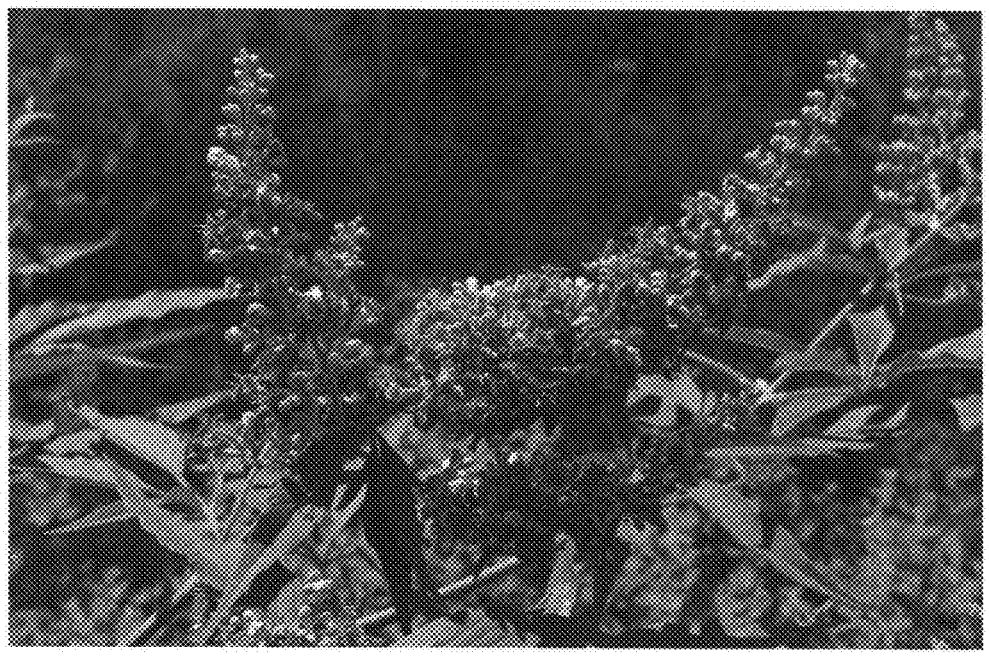
FIG. 2 Illustrates a close-up view of the inflorescences of 'PIIVAC-I'.

In the following description, color references are made to The Royal Horticultural Society Colour Chart, 2007 Edition, except where general terms of ordinary dictionary significance are used. The plant used for the description was approximately two years old and was grown in the ground in a nursery in Watkinsville, Ga. Colors are described using The Royal Horticultural Society Colour Chart (R.H.S.).

Botanical classification: *Vitex agnus-castus* L., cultivar 'PIIVAC-I'. Parentage: Female, or seed, parent: unnamed and unpatented seedling selection. Male, or pollen parent: unknown (open-pollinated). Propagation: terminal cuttings. Time to initiate roots, summer: about 28 days at 32° C.

Plant description: Deciduous flowering shrub; compact, rounded to upright-spreading growth habit. Freely branching; pruning enhances lateral branch development.

*Root description*.—Numerous, fibrous and well-branched.

*Plant size*.—About 147 cm high from the soil level to the top of the inflorescences and about 191 cm wide.

*First year stems*.—Have a diameter of about 3.5 mm. Shape: quadrangular when young, becoming rounded with age. Pubescence: tomentulose.

*Second year and older stems*.—Have a diameter of about 4 mm or more. Shape: round.

*Trunk diameter*.—5.7 cm at the soil line. Color: N200A.

*Internode length*.—About 5 cm.

*Strength*.—Flexible when young, becoming stronger with age.

*First year stem color* (*young*).—177A on the upper surface, 144B on the lower surface. Color (mature): upper and lower surfaces are N199A.

*Second year and older stem color*.—200D. Bark does not exfoliate.

Vegetative buds: Opposite arrangement, sessile, subglobose, 2 bud scales with tomentulose pubescence. Color: 145C. Size: about 1.5 mm in length and 1 mm in width.

Foliage description:

*Arrangement*.—Opposite, compound palmate, 5 to 7 leaflets.

*Leaflet length*.—About 8.2 cm.

*Leaflet width*.—About 1.6 cm.

*Shape*.—Elliptic-ovate to lanceolate.

*Apex*.—Acuminate.

*Base*.—Cuneate.

*Margin*.—Usually entire, occasionally few serrations. Foliage gives off a somewhat spicy odor when crushed.

*Texture*.—Upper surface is glabrous and matte, lower surface is tomentulose.

*Venation pattern*.—Pinnate.

*Venation color* (*upper surface*).—145A.

*Venation color* (*lower surface*).—145C.

*Foliage color* (*upper surface*).—N137B.

*Foliage color* (*lower surface*).—191A.

*Petiole length*.—About 4.6 cm.

*Petiole diameter*.—About 2 mm.

*Petiole color*.—Upper surface is 177A and lower surface is 144B.

*Pubescence*.—Tomentulose.

Flower description: Flowers on new growth. Flowers are produced from about June through September in Watkinsville, Ga. An inflorescence is showy for about two weeks, and individual flowers last about two days and are self-cleaning. Fragrance: none observed.

*Inflorescence type*.—Terminal panicles.

*Inflorescence length*.—About 10.3 cm.

*Inflorescence width*.—About 3.6 cm. An inflorescence contains approximately 88 individual flowers.

*Peduncle*.—About 9.3 cm in length, about 2 mm in diameter, color is 177A, with tomentulose pubescence.

*Individual flowers*.—About 1 cm in height and 1 cm in diameter.

*Flower buds*.—Length: about 6 mm; Diameter: about 2 mm; Color: 91 C.

*Pedicels*.—About 3 mm in length, less than 1 mm in diameter, 145C in color with tomentulose pubescence.

*Calyx*.—Consists of 5 fused sepals with acute apices and 145B in color. The calyx is about 4 mm in length, about 2 mm in diameter, 145B in color with tomentulose pubescence.

Petals:

*Arrangement/appearance*.—5 petals fused at the base to form the corolla tube, which is about 6 mm in length, 3 mm in width and 85B in color. The lower petal is cupped and larger than the other 4 petals which are reflexed.

*Lower petal*.—Length: about 5.5 mm. Width: about 4 mm. Shape: elongated. Apex: broad obtuse to rounded. Texture: glabrous.

*Upper and lateral petals*.—Length: about 3 mm. Width: about 2.5 mm. Shape: oblong. Apex: broad obtuse to rounded. Texture: glabrous.

*Petal color* (*all petals*).—Upper surface is N88A in color and lower surface is 85B in color.

Stamens:

*Quantity/arrangement*.—4 stamens per flower attached to the inner base of the corolla tube, about 5 mm long, filament color is 85CD, and anther color is 79A. The stamens are not pubescent. Pollen: produced in moderate quantities and is 158D in color.

Pistils:

*Quantity*.—One inferior pistil per flower.

*Pubescence*.—None.

*Pistil*.—About 1 cm in length and about 1.5 mm in width.

*Stigma shape*.—Forked, about 1 mm in width.

*Stigma color*.—84D.

*Style color*.—77D and about 8 mm in length.

*Ovary color*.—143C and about 1.5 mm in diameter.

Fruit:

*Type/appearance*.—Drupe, rounded to oblong in shape.

*Length*.—About 4 mm.

*Diameter*.—About 3 mm.

*Immature color*.—145B at the base and 178B at the apex.

*Mature color*.—N200B. Each drupe contains one seed that is about 3.5 mm long, 2.5 mm wide, and N199A in color.

Disease/pest resistance: Plants of the claimed *Vitex* variety grown in field and container trials have exhibited resistance to leaf spot. 'PIIVAC-I' is cold hardy in USDA Cold Hardiness Zones 6-9.

I claim:

1. A new and distinct *Vitex* plant named 'PIIVAC-I', as illustrated and described herein.

* * * * *